(12) United States Patent
Evans et al.

(10) Patent No.: US 9,757,268 B2
(45) Date of Patent: Sep. 12, 2017

(54) HIP SPICA CAST AND UNDERGARMENT FOR USE WITH HIP SPICA CAST

(71) Applicant: BSN medical, Inc., Charlotte, NC (US)

(72) Inventors: John C. Evans, Nr Rochdale (GB); Koen Jozef Maria Jorissen, Hamburg (DE)

(73) Assignee: BSN Medical, Inc., Charlotte, NC (US)

( * ) Notice: Subject to any disclaimer, the term of this patent is extended or adjusted under 35 U.S.C. 154(b) by 255 days.

(21) Appl. No.: 14/336,247

(22) Filed: Jul. 21, 2014

(65) Prior Publication Data
US 2016/0015550 A1  Jan. 21, 2016

(51) Int. Cl.
*A61F 5/00* (2006.01)
*A61F 5/058* (2006.01)

(52) U.S. Cl.
CPC .... *A61F 5/0585* (2013.01); *A61F 2210/0076* (2013.01)

(58) Field of Classification Search
CPC .......... A61F 5/04; A61F 5/058; A61F 5/0585; A61F 5/05841; A61F 13/041; A61F 2210/0085; A61F 2210/0076
USPC ............................... 602/3, 6, 7, 24
See application file for complete search history.

(56) References Cited

U.S. PATENT DOCUMENTS

| 4,800,872 | A | * | 1/1989 | Buese | ...................... | A61F 13/04 |
| | | | | | | 427/407.3 |
| 5,267,944 | A | | 12/1993 | Fraser | | |
| 2005/0043664 | A1 | | 2/2005 | Reaux | | |
| 2008/0178369 | A1 | | 7/2008 | Kitsch et al. | | |
| 2008/0269653 | A1 | | 10/2008 | Zhong | | |
| 2009/0126413 | A1 | * | 5/2009 | Sorensen | ................ | A61F 13/04 |
| | | | | | | 66/196 |
| 2012/0123377 | A1 | * | 5/2012 | Back | .................. | A61F 13/15699 |
| | | | | | | 604/385.01 |
| 2012/0220908 | A1 | * | 8/2012 | Evans | ................... | A61F 13/041 |
| | | | | | | 602/6 |

FOREIGN PATENT DOCUMENTS

| CA | 2 052 546 A1 | 3/1993 |
| WO | 93 10732 A1 | 6/1993 |
| WO | 2010 131840 A2 | 11/2010 |

OTHER PUBLICATIONS

ISA International Search Report dated Feb. 19, 2015 for PCT/US2014/048811.

* cited by examiner

*Primary Examiner* — Kim M Lewis
(74) *Attorney, Agent, or Firm* — Shumaker, Loop & Kendrick, LLP (57) ABSTRACT

An undergarment for use with a cast tape to form a hip spica cast, such as a pantaloon-type hip spica cast. The cast includes at least one layer of a 3D spacer synthetic padding material formed into a fabric of monofilament yarns and fabricated into an anatomically correct undergarment structure for being positioned around a torso and residing directly against the skin of a hip spica cast patient. At least one fabric perineal panel is attached to the undergarment in the perineal area of the undergarment and adapted for being positioned between the patient and an overlying cast material defining a perineal opening in the cast.

19 Claims, 6 Drawing Sheets

HIP SPICA CAST AND UNDERGARMENT FOR USE WITH HIP SPICA CAST

TECHNICAL FIELD AND BACKGROUND OF THE INVENTION

This invention relates to an undergarment formed of orthopedic padding, for example, for use as an undercast padding of the type used to protect and cushion the skin of a patient from the relatively rigid material of a cast, such as those constructed of plaster of Paris or synthetic cast tape. Specifically, this invention relates to a hip spica cast intended primarily for infants and other pediatric patients. The cast is constructed of an undercast padding material characterized by having a very open water and air transmissive structure enclosed within a very open water and air transmissive cast tape.

A cast which includes the torso of the body and one or more limbs is called a spica cast. A hip spica includes the torso of the body and one or more legs. A hip spica which covers only one leg to the ankle or foot may be referred to as a single hip spica, while one which covers both legs is called a double hip spica. A one-and-a-half hip spica encases one leg to the ankle or foot and the other to just above the knee. The extent to which the hip spica covers the torso depends greatly on the injury and the surgeon; the spica may extend only to the navel, allowing mobility of the spine and the possibility of walking with the aid of crutches, or may extend to the rib cage or even to the armpits in some rare cases. Hip spicas are used for a number of conditions and injuries, such as congenital hip dislocation or dysplasia.

In some cases, a hip spica may only extend down one or both legs to above the knee. Such casts, called pantaloon casts, are used to immobilize an injured lumbar spine or pelvis, in which case the torso portion of the cast usually extends upwardly to or just below the armpits. The specific example discussed in this application is such a pantaloon cast, but the invention is not limited to this particular type of cast.

A traditional hip spica cast is constructed from a simple stockinette and padding material made from cotton or synthetic fibers, and offers poor or no water resistant capability. Cotton and some synthetic padding actually absorb and retain large quantities of water. A hip spica cast is typically worn for a period of 6-10 weeks. During this period of time, traditional casts having a water-absorbent stockinette can promote skin maceration and discomfort. This is a particular problem with infants and very small children who are incontinent and therefore are far more likely to soil the cast with urine and feces. To facilitate toileting or diaper changing and hygienic cleaning, an opening, referred to as the "perineal opening", is typically created in the cast at the groin. It is formed either during cast application or after cast application by cutting the hole with a cast saw. The opening must then be petalled or lined to keep this area of the cast clean and dry. However, this is difficult, particularly with infants and small children. In reality, within a relatively short period of time after traditional hip spica cast application, the area around the perineal opening becomes soiled with urine and feces and develops foul odors that must be tolerated or masked with various deodorizers for a month or more. Rashes, maceration, skin and systemic infections, open sores and other conditions may retard the treatment schedule and impose pain and discomfort on the infant or pediatric patient.

The present invention provides a more conformable, water-resistant product that permits the material to be formed into an anatomically-shaped and sized undergarment that can be donned onto the patient, and then enclosed by wrapping with a suitable water and air permeable synthetic cast tape to form the spica cast. The perineal area of the garment includes protective panels of fabric that are incorporated into the garment and which can be pulled out of the garment and folded around the hardened part of the outer cast to prevent rubbing, particularly when a diaper is pushed through the perineal opening from the outside.

One of the problems with conventional cast padding as well as commercially available water resistant padding is that the padding collapses underneath a cast over the duration of 4-6 weeks as water and perspiration are absorbed into the structure. This reduction in thickness and resultant increase in density retards moisture transfer by both wicking and evaporation, and lessens the protection offered by the padding.

The hip spica cast according to the present invention accommodates bathing, showering and contact with water for cleansing while permitting surface moisture to be dried, and moisture on the interior of the hip spica cast to evaporate relatively quickly, leaving the patient dry and comfortable. For smaller patients, the patient can be held in proximity to, for example, a handheld spray nozzle and the cast sprayed with a gentle spray of warm, cleansing water. Urine is readily washed away, and feces are dissolved, diluted and allowed to drain away. The patient is left clean and odor-free. Excess surface water is easily blotted away with an absorbent cloth or paper towel, and water on the interior evaporates within about one hour. This process can be repeated as necessary during the entire treatment period. Moreover, because of the ability to cleanse the patient as described above, it may not be necessary to provide the perineal opening in some instances.

SUMMARY OF THE INVENTION

Therefore, it is an object of the invention to provide a hip spica cast formed from a water and air permeable padding material formed into a garment, and enclosed within a water and air permeable synthetic cast tape. It is another object of the invention to provide an orthopedic padding that is comfortable when worn under a synthetic cast.

It is another object of the invention to provide a hip spica cast in the form of a garment that is relatively thin but still providing sufficient cushioning and thus provides a low profile undercast layer when properly overlapped during application.

It is another object of the invention to provide a hip spica cast that is relatively open and therefore breathable.

It is another object of the invention to provide a hip spica cast that is resistant to collapse during extended use.

It is another object of the invention to provide a hip spica cast that promotes drainage of water from the cast when wetting occurs.

It is another object of the invention to provide a breathable hip spica cast that is comfortable when worn against the skin under a wrapping of synthetic cast tape.

It is another object of the invention to provide a breathable hip spica cast that includes perineal panels that protect the wearer from contact with the hard outer cast material, and prevent rubbing and chafing when a diaper is being inserted into the cast through the perineal opening.

These and other objects of the present invention are achieved by providing an undergarment for use with a cast tape to form a hip spica cast, and comprising

BRIEF DESCRIPTION OF THE DRAWINGS

Some of the objects of the invention have been set forth above. Other objects and advantages of the invention will appear as the invention proceeds when taken in conjunction with the following drawings, in which.

DETAILED DESCRIPTION OF PREFERRED EMBODIMENT OF THE INVENTION AND BEST MODE

Referring now specifically to the drawings, a hip spica undergarment 10 is shown. The particular hip spica undergarment 10 is a pantaloon hip spica that extends from below the armpits of the patient to above the knees, particularly intended for infants and small children. As noted above, there are other types of hip spica casts, and those are included within the scope of the invention even though not further described. The undergarment 10 includes a torso 12 and two integrally-formed legs 14 and 16 that are constructed of front and back blanks 18 and 20 of padding material that are connected to form the undergarment 10 as shown. The seams of the undergarment 10 may be formed by any suitable method, such as ultrasonic welding, butt or overedge seaming, or with an adhesive, either in tape or atomized glue form.

Each leg 14 and 16 is formed of double layers of fabric that form front and back blanks 18A, 18B, 20A, 20B, respectively. The undergarment 10 also includes a pair of fabric outer side gussets 22 and 24 inserted between the pairs of layers 18A, 18B and 20A, 20B respectively, as shown, that extend along the distal aspects of the undergarment 10 from the waist opening 26 to the leg openings 28, 30. Similarly, an inner gusset 36 is inserted between the pairs of fabric layers 18A, 18B and 20A, 20B respectively, as shown, and extends in a curved proximal configuration up each leg 14, 16 and across the perineal area.

Preferably, the undergarment 10 is provided with locator markings to indicate to the technician the location and size of a perineal opening. The markings may indicate a perineal area 32 outlined with a contrasting color, stitching or any other suitable indicator. Alternatively, a perineal opening may be preformed in the undergarment 10 when constructed.

Figure 1:
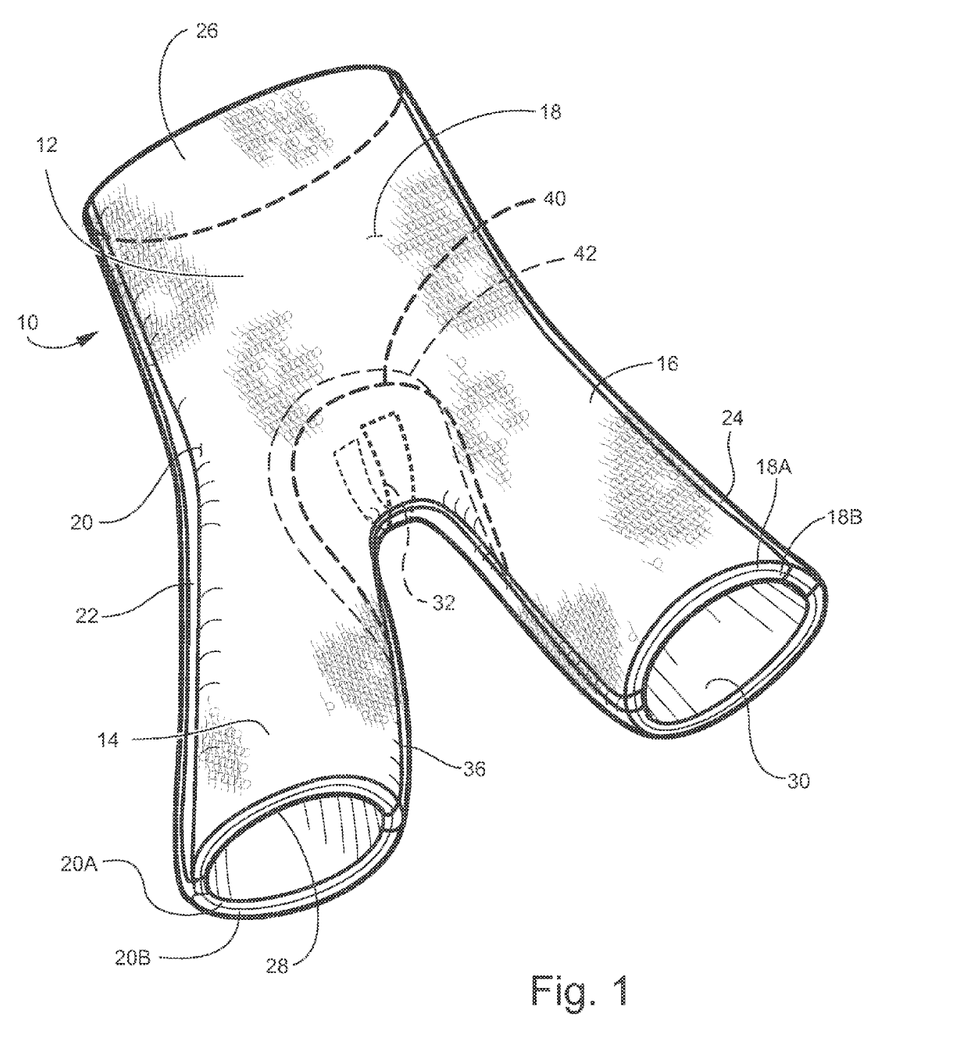
FIG. 1 is a perspective view of a hip spica cast undergarment according to one embodiment of the invention.
Figure 2:
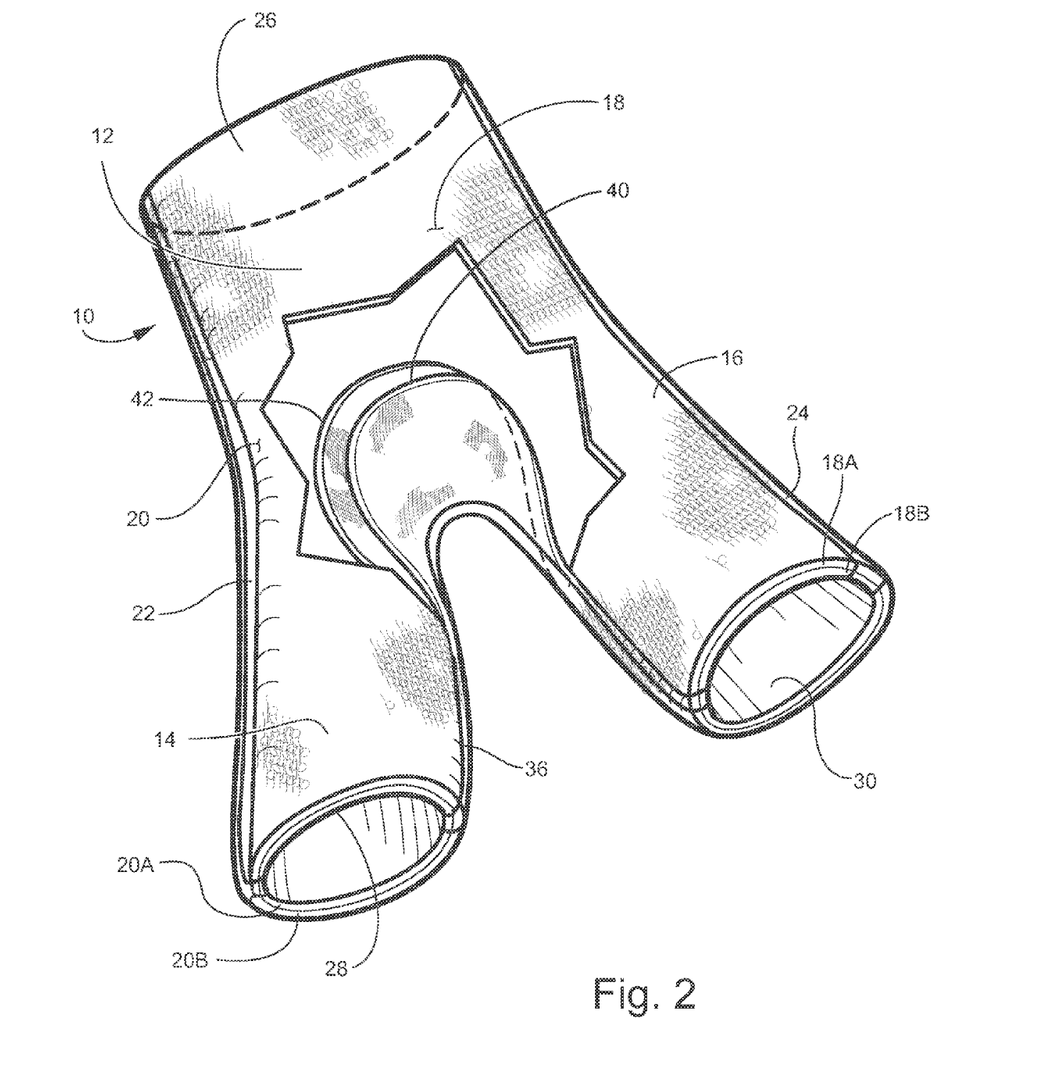
FIG. 2 is a perspective view of the hip spica cast undergarment according to FIG. 1 with parts broken away to reveal protective perineal panels.

As best shown by reference to FIGS. 1 and 2, fabric front and rear protective panels 40 and 42 are attached to the inside of the undergarment 10 and extend laterally across the perineal area 32 and partially down legs 14, 16. The front panel 40 is interconnected with the gusset 36 and the front leg blanks 18A, 20A, and the rear panel 42 is interconnected with the gusset 36 and the rear leg blanks 18B, 20B. Therefore, a space the width of the inner gusset 36 is left between the front and rear panels 40 and 42 in the perineal area. Note that the panels 40, 42 are generally curved with the greatest dimension in the perineal area 32, tapering as they extend down the legs 14, 16.

To apply the undergarment 10, the patient is positioned in the undergarment 10 through the waist opening 26 with its legs extending through respective leg openings 28, 30.

The double layers of fabric forming the front and back blanks 18A, 18B and 20A, 20B provide enhanced comfort while still providing a moisture vapor transmission rate (MVTR) of over 1000 g/m$^2$/24 hrs. Other embodiments may include single thickness or three or more thicknesses of the undergarment material. The front and back blanks 18A, 18B and 20A, 20B are preferably formed of 4-6 mm thick 3D Knitted material with a pillar stitch 0.07 mm polyester with an inlay of 100 decitex 72 filament polypropylene. The multifilament polypropylene yarn of the inlay acts as a barrier to any leaching of resin on the infant's skin.

The gussets 22, 24 and 36 are fabricated of 100 percent polypropylene monofilament having a diameter of 0.1 mm to 0.3 mm. The thickness of the fabric is 3-4 mm.

The layers of fabric shown in FIGS. 1 and 2 can be constructed using any suitable hydrophobic/water resistant monofilament or multifilament yarn such as polypropylene, polyester, polyethylene and nylon to provide sufficient cushioning and breathability.

Preferably, the structure of the undergarment 10 should provide some stretch in both the length-wise and width-wise directions, and facilitate conforming the undergarment 10 around an anatomical shape during application. The undergarment 10 can be fabricated in a length to cover all or part of the torso and leg or legs of the patient, as medically required.

The fabric of the undergarment 10 can be treated with one or more finishes to provide additional water resistance, anti-bacterial and/or anti-odor characteristics, or aromatherapy to improve the functionality or enhance the cast-wearing experience for the patient. Alternatively, the padding material can be fabricated from modified/treated monofilament yarns incorporating suitable fillers or finishes to improve the performance.

Figure 3:
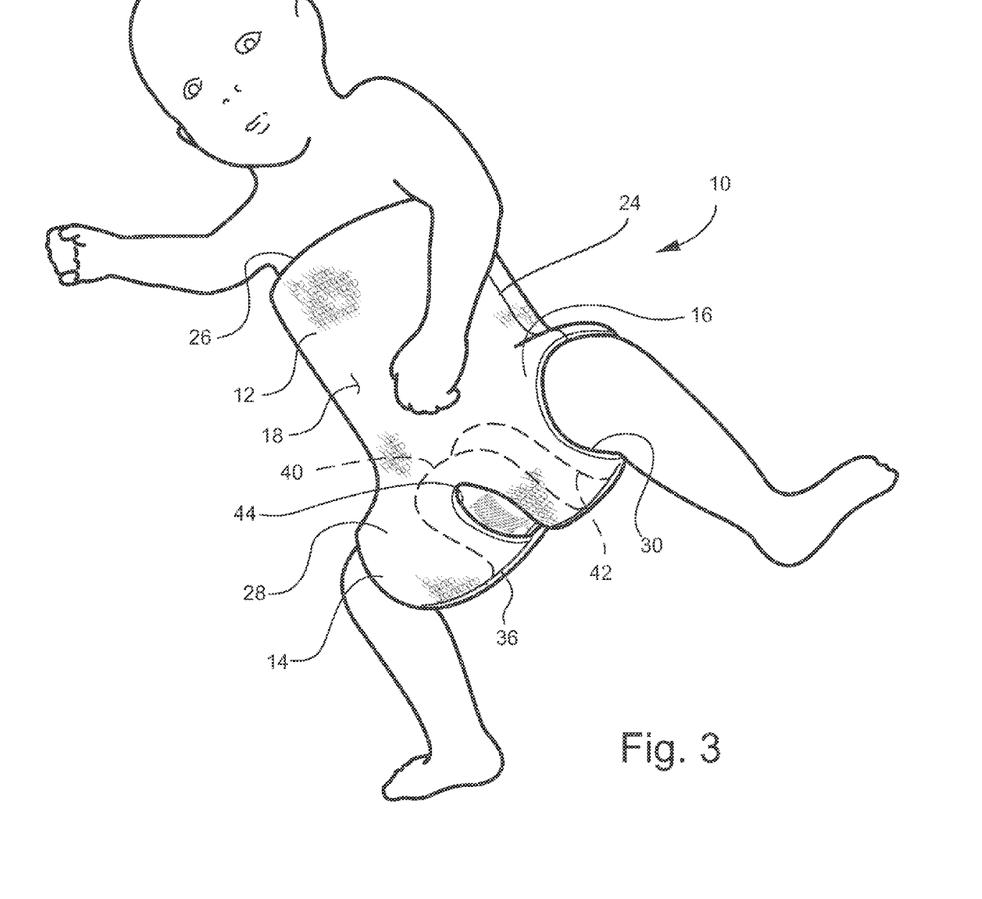
FIG. 3 is an environmental view showing a hip spica cast undergarment in place on an infant.

Referring now to FIG. 3, and by way of example, the undergarment 10 of FIG. 3 is applied to the infant by donning it over the legs and up across the torso to the medically-appropriate position—generally at or just below the armpits. As noted above, the stretch provided by the undergarment 10 permits a fast, accurate, closely-conforming application without wrinkles or creases. No stockinette or other material is used underneath the undergarment 10. It resides directly against the skin. A perineal opening 44 is either preformed in the undergarment 10 or formed during application.

Figure 4:
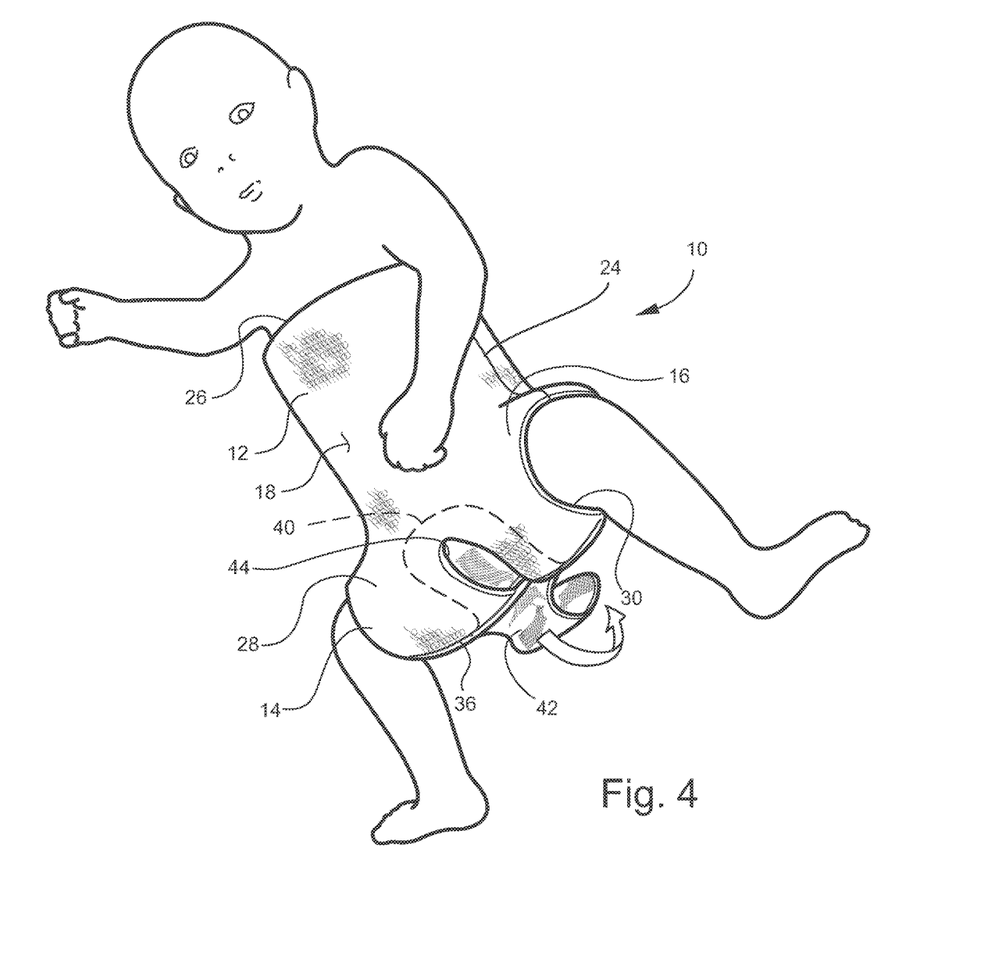
FIG. 4 is a view similar to FIG. 3 showing the front and rear perineal panels pulled to the outside of the undergarment.
Figure 5:
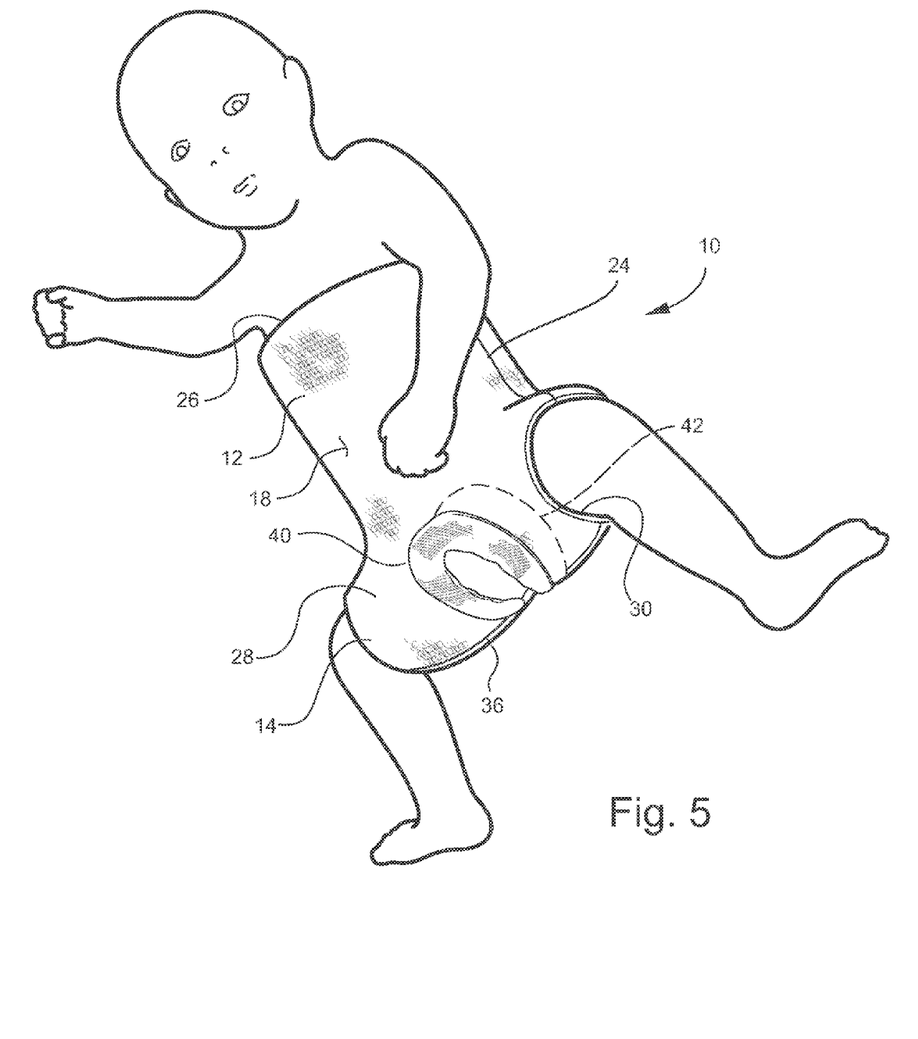
FIG. 5 is a view similar to FIG. 4 showing the front and rear perineal panels pulled to the outside of the undergarment.

Referring now to FIGS. 4 and 5, after the undergarment 10 is placed on the infant the protective panels 40 and 42, which are originally on the interior of the undergarment 10, are pulled through the perineal opening 44 from the inside to the outside. The front panel 40 resides around the front end of the perineal opening 44 and the rear panel 42 resides around the rear end of the perineal opening 44.

Figure 6:
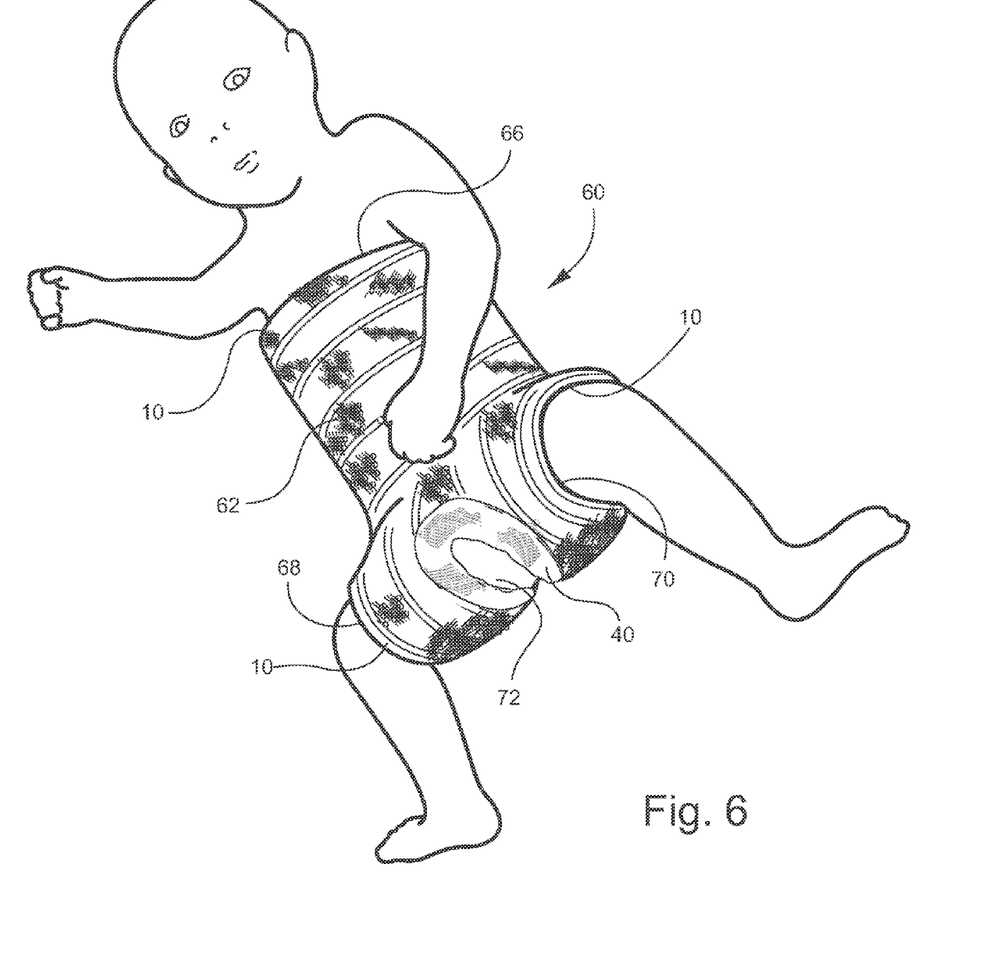
FIG. 6 is a view showing the hip spica cast after cast tape has been applied over the undergarment with the perineal panels pulled to the outside to cover the cast edges in the perineal area.

As is shown in FIG. 6, after application of the undergarment 10, an over cast 60 is formed by wrappings of synthetic cast tape 62. The preferred cast tape is Delta-Cast® brand synthetic fiber cast tape or Delta-Lite® brand fiberglass cast tape manufactured and sold by BSN medical, Inc. and BSN medical, GmbH. These cast tapes are supplied in various widths, the particular width being a choice left to the physician or cast technician. Two-inch or three-inch cast tape is the most often used. The cast tape 62 is removed from its moisture impervious pouch, wetted, and excess water removed by wringing the cast tape 62 while wrapped in an absorbent towel. The cast tape 62 is then applied over the undergarment 10 by wrapping the cast tape 62 circumferentially around the patient, taking care in the usual manner to properly overlap adjacent wraps, eliminate wrinkles and puckers and leaving a short width of exposed undergarment at a top opening 66, leg openings 68 and 70, and the perineal opening 72, which is aligned and communicates with the perineal opening 44 in the undergarment 10. The result is the cast 60 shown in FIG. 6.

Formation of the perineal opening 72 in the cast leaves a rough, hard edge. The front and rear panels 40, 42 are then pulled front inside the cast 60 through the perineal opening 72 and arranged to overlie the edges of the perineal opening 72, thereby providing a protective covering that will prevent chaffing, abrasion and irritation to the tender skin of the upper inner legs and adjacent genital area.

The specific manner of application of the cast tape is a matter of medical procedure. One such procedure, illustrated with a prior art application of an underwrapping of strips of padding material, is contained in Application Manual-Hip Spica Cast, published by BSN medical, Inc., ©BSN medical, Inc., 2011, at pages 10-16.

The cast tape 62 hardens in several minutes to form the rigid cast 60 as shown in FIG. 6 that is nevertheless very water and air permeable. Typically, the torso portion of the cast 60 can be covered in a soft cloth or garment, or the patient's arms covered in a soft garment, in order to prevent chafing of the patient's arms against the outer surface of the cast tape 62 on the torso portion of the cast 60.

For infant or small juvenile patients, the patient can be held in proximity to, for example, a handheld spray nozzle and the cast sprayed with a gentle spray of warm, cleansing water. Urine is readily washed away, and feces are dissolved, diluted and allowed to drain away. The patient is left clean and odor-free. Excess surface water is easily blotted away with an absorbent cloth or paper towel, and water on the interior evaporates within about one hour. This process can be repeated as necessary during the entire treatment period. Moreover, because of the ability to cleanse the patient as described above, it may not be necessary to provide the perineal opening in some instances.

An undergarment for use in forming a hip spica cast, and a hip spica cast according to the invention have been described with reference to specific embodiments and examples. Various details of the invention may be changed without departing from the scope of the invention. Furthermore, the foregoing description of the preferred embodiments of the invention and best mode for practicing the invention are provided for the purpose of illustration only and not for the purpose of limitation, the invention being defined by the claims.

We claim:

1. A water and air permeable undergarment for use with a cast tape to form a water and air permeable hip spica cast, and comprising:
   (a) at least one layer of a fabric formed of synthetic yarns and fabricated into an anatomically correct undergarment structure having a torso portion and first and second leg portions for being positioned onto a torso and legs, and adapted to reside directly against the skin of, a hip spica cast patient;
   (b) a perineal area at a lower extremity of the torso portion between the first and second legs; and
   (c) a fabric perineal panel attached to the undergarment in the perineal area of the undergarment and adapted for being positioned between the patient and an overlying cast material defining a perineal opening in the cast, wherein:
   the undergarment has a torso portion including a top opening for being positioned on a torso portion of the patient and at first and second leg portions terminating in respective leg openings adapted to reside between the hips and knees of the patient, and wherein the undergarment is formed of first and second overlaid padding layers defining an anterior side of the undergarment and third and fourth overlaid padding layers defining a posterior side of the undergarment, each padding layer being water and air permeable.

2. A water and air permeable undergarment according to claim 1, wherein the undergarment has at least one integrally-formed leg portion.

3. A water and air permeable undergarment according to claim 1, wherein the undergarment has a torso portion including a top opening for being positioned on a torso portion of the patient and at least one integrally-formed leg portion terminating in a leg opening adapted to reside between a hip and knee of the patient.

4. A water and air permeable undergarment according to claim 1, wherein the undergarment has a torso portion including a top opening for being positioned on a torso portion of the patient and a first leg portion and second leg portion that terminate in respective leg openings adapted to reside between the hips and knees of the patient.

5. A water and air permeable undergarment according to claim 1, wherein the first and second padding layers and the third and fourth padding layers are joined with monofilament yarns along left and right seam lines extending from a top opening to first and second leg openings at a lowermost terminus of the undergarment.

6. A water and air permeable undergarment according to claim 5, wherein the monofilament yarns are thermoplastic and the seam lines are formed by a seaming process selected from the group consisting of ultrasonic energy, butt seaming, overedge seaming, joining with an adhesive tape and joining in with an atomized glue.

7. A water and air permeable undergarment according to claim 6, wherein the undergarment includes a perineal opening.

8. A water and air permeable undergarment according to claim 7, wherein the undergarment is configured to form an undergarment for a pantaloon hip spica cast.

9. A water and air permeable undergarment according to claim 1, wherein the cast tape is selected from the group consisting of a synthetic fiber or fiberglass/non fiberglass substrate coated or saturated with a moisture-curable resin and stored in a flexible condition in a moisture impervious package until use, at which time removal of the cast tape from the moisture impervious package and exposure to moisture causes the substrate to harden over a time period sufficiently long to allow application of the cast tape while still flexible over the undergarment.

10. A water and air permeable undergarment for use with cast tape to form a hip spica cast, and comprising:
   a 3D spacer synthetic material that is water and air permeable and formed into a knitted fabric of monofilament yarns, the undergarment comprising a plurality of a knitted fabrics with each fabric fabricated into an anatomically appropriate undergarment structure with a first knitted fabric forming an innermost layer and being positioned in a second knitted fabric forming an outermost layer, the first knitted fabric adapted to reside directly against the skin of a hip spica cast patient; wherein:

each fabric of the padding material is formed with 200-850 courses per meter; and the padding material weighs between 50-400 g/m² and has a nominal thickness when not compressed or under tension of approximately 1.5-3.5 mm.

11. A water and air permeable undergarment according to claim 10, wherein the undergarment has a torso portion including a top opening for being positioned on a torso portion of the patient and at first and second leg portions terminating in respective leg openings adapted to reside between a hip and knee of the patient, and wherein the undergarment is formed of first and second overlaid padding layers defining an anterior side of the undergarment and third and fourth overlaid padding layers defining a posterior side of the undergarment.

12. A water and air permeable undergarment according to claim 11, wherein the first and second padding layers and the third and fourth padding layers are joined along left and right seam lines extending from a top opening to first and second leg openings at a lowermost terminus of the undergarment.

13. A water and air permeable undergarment according to claim 10, wherein the padding material weighs between 100-250 g/m².

14. A water and air permeable hip spica cast, comprising:
(a) a water and air permeable undergarment comprising a padding layer formed of a 3D spacer synthetic padding material that is water and air permeable and formed into a fabric of monofilament yarns and fabricated into an anatomically correct undergarment structure for being positioned around a torso and adapted to reside directly against the skin of a hip spica cast patient;
(b) a cast tape is selected from the group consisting of a synthetic fiber or fiberglass/non fiberglass substrate coated or saturated with a moisture-curable resin and stored in a flexible condition in a moisture impervious package until use, at which time removal of the cast tape from the moisture impervious package and exposure to moisture causes the substrate to harden over a time period sufficiently long to allow application of the cast tape while still flexible over the undergarment; and
(c) the cast tape adapted to be positioned circumferentially over the undergarment and around the torso of the patient, wherein:

the undergarment has a torso portion including a top opening for being positioned on a torso portion of the patient and at first and second leg portions terminating in respective leg openings adapted to reside between a hip and knee of the patient, and wherein the undergarment is formed of first and second overlaid padding layers defining an anterior side of the undergarment and third and fourth overlaid padding layers defining a posterior side of the undergarment.

15. A water and air permeable hip spica cast according to claim 14, wherein the first and second padding layers and the third and fourth padding layers are joined along left and right seam lines extending from a top opening to first and second leg openings at a lowermost terminus of the undergarment.

16. A water and air permeable hip spica cast according to claim 14, wherein the padding material weighs between 100-250 g/m².

17. A water and air permeable hip spica cast according to claim 14, wherein the monofilament yarns are thermoplastic and the seam lines are formed by a seaming process selected from the group consisting of ultrasonic energy, butt seaming, overedge seaming, joining with an adhesive tape and joining in with an atomized glue.

18. A water and air permeable hip spica cast according to claim 14, wherein the undergarment includes a perineal opening.

19. A water and air permeable hip spica cast according to claim 14, wherein:
(a) the 3D spacer synthetic padding material is formed into a knitted fabric of monofilament yarns, the undergarment comprising a plurality of a knitted fabrics with each fabric fabricated into an anatomically appropriate undergarment structure with a first knitted fabric forming an innermost layer and being positioned in a second knitted fabric forming an outermost layer, the first knitted fabric adapted to reside directly against the skin of a hip spica cast patient;
(b) wherein each fabric of the padding material is formed with 200-850 courses per meter; and
(c) the padding material weighs between 50-400 g/m² and has a nominal thickness when not compressed or under tension of approximately 1.5-3 5 mm.

* * * * *